United States Patent
Ghoshal et al.

(10) Patent No.: US 7,893,399 B2
(45) Date of Patent: Feb. 22, 2011

(54) METHODS FOR DETECTING DEHYDROEPIANDROSTERONE BY MASS SPECTROMETRY

(75) Inventors: Amit Ghoshal, Ladera Ranch, CA (US);
Nigel J. Clarke, Oceanside, CA (US);
Richard E. Reitz, San Clemente, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 142 days.

(21) Appl. No.: 12/207,428

(22) Filed: Sep. 9, 2008

(65) Prior Publication Data
US 2010/0059671 A1   Mar. 11, 2010

(51) Int. Cl.
*B01D 59/44* (2006.01)
(52) U.S. Cl. ................. 250/282; 250/281; 250/288
(58) Field of Classification Search ............. 250/281, 250/282
See application file for complete search history.

(56) References Cited

U.S. PATENT DOCUMENTS

| | | | |
|---|---|---|---|
| 5,772,874 A | 6/1998 | Quinn et al. | |
| 5,795,469 A | 8/1998 | Quinn et al. | |
| 5,919,368 A | 7/1999 | Quinn et al. | |
| 5,968,367 A | 10/1999 | Quinn et al. | |
| 6,107,623 A | 8/2000 | Bateman et al. | |
| 6,124,137 A | 9/2000 | Hutchens et al. | |
| 6,204,500 B1 | 3/2001 | Whitehouse et al. | |
| 6,268,144 B1 | 7/2001 | Köster | |
| 6,905,714 B2 * | 6/2005 | Ong et al. | 424/769 |
| 6,977,143 B1 * | 12/2005 | Caulfield et al. | 435/4 |
| 7,439,026 B2 * | 10/2008 | Pandian et al. | 435/7.1 |
| 7,473,560 B2 | 1/2009 | Soldin | |
| 2008/0128606 A1 * | 6/2008 | Grant et al. | 250/282 |
| 2009/0104624 A1 * | 4/2009 | Pandian et al. | 435/7.1 |
| 2010/0059671 A1 * | 3/2010 | Ghoshal et al. | 250/282 |
| 2010/0084546 A1 * | 4/2010 | Ghoshal et al. | 250/282 |

OTHER PUBLICATIONS

Bartolucci et al., Liquid chromatography tandem mass spectrometric quantitation of sulfamethazine and its metabolites: direct analysis of swine urine by triple quadrupole and by ion trap mass spectrometry, *Rapid Commun. Mass Spectrom.* 14:967-973 (2000).

Chatman, et al., Nanoelectrospray Mass Spectrometry and Precursor Ion Monitoring for Quantitative Steroid Analysis and Attomole Sensitivity, *Anal. Chem.* 71:2358-2363 (1999).

Dimitrakov et al., Adrenocortical Hormone Abnormalities in Men with Chronic Prostatitis/Chronic Pelvic Pain Syndrome, *Urology* 71:261-266 (2008).

Gonzalo-Lumbreras et al., Solvent and solid-phase extraction of natural and synthetic anabolic steroids in human urine, *J Chromatogr B Biomed Sci Appl.* 754(2):419-425 (2001).

(Continued)

*Primary Examiner*—David A Vanore
(74) *Attorney, Agent, or Firm*—Foley & Lardner LLP (57) ABSTRACT

Provided are methods for determining the amount of underivatized dehydroepiandrosterone (DHEA) in a sample using mass spectrometry. The methods generally involve ionizing DHEA in a sample and detecting and quantifying the amount of the ion to determine the amount of DHEA in the sample.

26 Claims, 5 Drawing Sheets

OTHER PUBLICATIONS

Guo, et al., Steroid Profiles Using Liquid Chromatography—Tandem Mass Spectrometry With Atmospheric Pressure Photoionization Source, *Arch Pathol Lab Med* 128:469-75 (2004).

Guo, et al., Simultaneous determination of 12 steroids by isotope dilution liquid chromatography-photospray ionization tandem mass spectrometry, *Clinica Chimica Acta* 372:76-82 (2006).

Higashi, et al., Determination of salivary dehydroepiandrosterone using liquid chromatography—tandem mass spectrometry combined with charged derivatization, *J Chromatogr B* 195-201 (2007).

Hoist et al., Use of Steroid Profiles in Determining the Cause of Adrenal Insufficiency, Steroids, 72(1):71-84 (2007).

Hsing, et al., Reproducibility of Serum Sex Steroid Assays in Men by RIA and Mass Spectrometry, *Cancer Epidemiol Biomarkers Prey* 16(5):1004-8 (2007).

Koplowitz, P. and Soldin, S.J., Steroid Profiles in Serum by Liquid Chromatography-Tandem Mass Spectrometry in Infants with Genital Hair, *J Pediatric Endocr Metab*. 20(5):597-605 (2007).

Labrie, et al., Bioavailability and metabolism of oral and percutaneous dehydroepiandrosterone in postmenopausal women, *J Steroid Biochem Mol Biol* 107:57-69 (2007).

Lafaye et al., Profiling of sulfoconjugates in urine by using precursor ion and neutral loss scans in tandem mass spectrometry. Application to the investigation of heavy metal toxicity in rats. Mass Spectrom. 39(6):655-664 (2004).

Liu, et al., Neurosteroids in Rat Brain: Extraction, Isolation, and Analysis by Nanoscale Liquid Chromatography-Electrospray Mass Spectrometry, *Anal Chem* 75:5835-46 (2003).

Luu-The et al., Steroid metabolism and profile of steroidogenic gene expression in Episkin™: High similarity with human epidermis, J Steroid Biochemistry & Molecular Biology 107:30-36 (2007).

Merchant, M. and Weinberger, S.R., Recent advancements in surface-enhanced laser desorption/ionization-time of flight-mass spectrometry, *Electrophoresis* 21:1164-1167 (2000).

Mitamura et al., Simultaneous determination of androstenediol 3-sulfate and dehydroepiandrosterone sulfate in human serum using isotope diluted liquid chromatography-electrospray ionization-mass spectrometry, J Chromatogr B Analyt Technol Biomed Life Sci. 796(1):121-130 (2003).

Newman et al., Analysis of steroids in songbird plasma and brain by coupling solid phase extraction to radioimmunoassay, Gen Comp Endocrinol. 155(3):503-510 (2008).

Polson et al., Optimization of protein precipitation based upon effectiveness of protein removal and ionization effect in liquid chromatography-tandem mass spectrometry, *Journal of Chromatography B* 785:263-275 (2003).

Robb et al., Atmospheric Pressure Photoionization: An Ionization Method for Liquid Chromatography-Mass Spectrometry, *Anal. Chem.* 72(15): 3653-3659 (2000).

Shackleton et al., Dehydroepiandrosterone sulfate quantification in serum using high-performance liquid chromatography/mass spectrometry and a deuterated internal standard: a technique suitable for routine use or as a reference method, Steroids, 55:472-478 (1990).

Holst et al., Steroid hormones: relevance and measurement in the clinical laboratory, Clin Lab Med 24:105-118 (2004).

Strahm et al., Isolation and quantification by high-performance liquid chromatrography-ion-trap mass spectrometry of androgen sulfoconjugates in human urine, J Chromatogr A. pp. 1196-1197, Jul. 4, 2008.

Wright et al., Proteinchip® surface enhanced laser desorption/ionization (SELDI) mass spectrometry: a novel protein biochip technology for detection of prostate cancer biomarkers in complex protein mixtures, *Prostate Cancer and Prostatic Diseases* 2:264-76 (1999).

Zimmer et al., Comparison of turbulent-flow chromatography with automated solid-phase extraction in 96-well plates and liquid-liquid extraction used as plasma sample preparation techniques for liquid chromatography-tandem mass spectrometry, *J Chromatogr A* 854: 23-35 (1999).

Zou, et al., Detection of dehydroepiandrosterone and androsterone in a traditional Chinese herbal product, *Food Addit Contam* 24(12):1326-33 (2007).

\* cited by examiner

METHODS FOR DETECTING DEHYDROEPIANDROSTERONE BY MASS SPECTROMETRY

FIELD OF THE INVENTION

The invention relates to the detection of dehydroepiandrosterone (DHEA). In a particular aspect, the invention relates to methods for detecting dehydroepiandrosterone by mass spectrometry.

BACKGROUND OF THE INVENTION

The following description of the background of the invention is provided simply as an aid in understanding the invention and is not admitted to describe or constitute prior art to the invention.

Dehydroepiandrosterone (DHEA) [(3β-hydroxy-5-androsten-17-one)] is a weak androgen synthesized by the adrenal cortex. It has a short plasma half-life and is usually converted to dehydroepiandrosterone sulfate (DHEA-S). Excessive DHEA secretion can produce acne, hirsutism and virilization via conversion to testosterone.

Mass spectrometric methods for measuring DHEA in a sample have been reported. See, e.g., Chatman, K., et al., *Anal Chem* 1999, 71:2358-63; Liu, S., et al., *Anal Chem* 2003, 75:5835-46; Higashi, T., et al., *J Chromatogr B* 2007, 195-201; Hsing, A., et al., *Cancer Epidemiol Biomarkers Prev* 2007, 16:1004-8; Labrie, F., et al., *J Steroid Biochem Mol Biol* 2007, 107:57-69; Guo, T., et al., *Arch Pathol Lab Med* 2004, 128:469-75; Guo, T., et al., *Clinica Chemica Acta* 2006, 372: 76-82; and Zou, P., et al., *Food Addit Contam* 2007, 24:1326-33. Guo, T., et al. and Zou, P., et al. recently reported liquid chromatography-tandem mass spectrometry techniques of measuring DHEA in a sample by observation of mass transitions from a precursor ion with a mass to charge ratio of 271 to a fragment ion with a mass to charge ratio of 213, and a precursor ion with a mass to charge ratio of 289.2 to a fragment ion with a mass to charge ratio of 270.9, respectively.

SUMMARY OF THE INVENTION

The present invention provides methods for detecting the amount of dehydroepiandrosterone (DHEA) in a sample by mass spectrometry, including tandem mass spectrometry. Preferably, the methods of the invention do not include derivatizing DHEA in a sample prior to the mass spectrometry analysis.

In one aspect, methods are provided for determining the amount of underivatized dehydroepiandrosterone (DHEA) in a test sample. Methods of this aspect include: (a) ionizing DHEA from a test sample to produce one or more DHEA ions detectable by mass spectrometry, wherein the produced ions comprise one or more ions selected from the group consisting of ions with a mass/charge ratio of $253.10 \pm 0.50$, $197.13 \pm 0.50$, and $167.10 \pm 0.50$; and (b) detecting the amount of one or more DHEA ions by mass spectrometry. Once the amount of the one or more DHEA ions is measured, the amount of DHEA ion(s) is related to the amount of DHEA in the test sample. In some embodiments, the mass spectrometry is tandem mass spectrometry. In some embodiments, the methods further comprise purifying DHEA in a test sample prior to mass spectrometry. In related embodiments, purifying comprises purifying DHEA in a test sample by liquid chromatography; preferably high performance liquid chromatography (HPLC). In some embodiments, purifying DHEA in a test sample comprises purifying by high turbulence liquid chromatography (HTLC), followed by high performance liquid chromatography (HPLC); preferably with on-line processing. In some embodiments, the test sample is body fluid; preferably plasma or serum. In some embodiments, the step of ionizing DHEA includes generating a precursor ion with a mass/charge ratio of $253.10 \pm 0.50$ and generating one or more fragment ions selected from the group consisting of ions with a mass/charge ratio of $197.13 \pm 0.50$ and $167.10 \pm 0.50$. In some embodiments, the methods have a limit of quantitation greater than or equal to 10 ng/dL but less than or equal to 2000 ng/dL. In some embodiments, the amount of one or more DHEA ions detected by mass spectrometry is related to the presence or amount of DHEA in a test sample by comparison to an internal standard; preferably 2, 2, 4, 6, 6-$d_5$ testosterone. The features of the embodiments listed above may be combined without limitation for use in methods of the present invention.

In a second aspect, methods are provided for determining the amount of underivatized dehydroepiandrosterone (DHEA) in a test sample by mass spectrometry. Methods of this aspect include: (a) purifying DHEA in a test sample with high turbulence liquid chromatography (HTLC); (b) ionizing DHEA from the test sample to produce one or more DHEA ions detectable by mass spectrometry; and (c) detecting the amount of one or more DHEA ions by mass spectrometry. In these methods, the amount of the DHEA ion(s) detected by mass spectrometry is related to the amount of DHEA in the test sample. In some embodiments, the mass spectrometry is tandem mass spectrometry. In some embodiments, purifying DHEA in a test sample comprises purifying with high performance liquid chromatography (HPLC). In related embodiments, HTLC and HPLC may be configured for on-line processing. In some embodiments, the test sample is a body fluid sample; preferably plasma or serum. In some embodiments, the DHEA ions detectable by mass spectrometry include one or more ions selected from the group consisting of ions with a mass/charge ratio of $253.10 \pm 0.50$, $197.13 \pm 0.50$, and $167.10 \pm 0.50$. In some embodiments, the step of ionizing DHEA includes generating a precursor ion with a mass/charge ratio of $253.10 \pm 0.50$ and generating one or more fragment ions selected from the group consisting of ions with a mass/charge ratio of $197.13 \pm 0.50$ and $167.10 \pm 0.50$. In some embodiments, the methods have a limit of quantitation greater than or equal to 10 ng/dL but less than or equal to 2000 ng/dL. In some embodiments, the amount of one or more DHEA ions detected by mass spectrometry is related to the presence or amount of DHEA in a test sample by comparison to an internal standard; preferably 2, 2, 4, 6, 6-$d_5$ testosterone. The features of the embodiments listed above may be combined without limitation for use in methods of the present invention.

In at third aspect, methods are provided for determining the amount of underivatized dehydroepiandrosterone (DHEA) in a test sample by tandem mass spectrometry. Methods of this aspect include: (a) purifying DHEA from the test sample by high turbulence liquid chromatography (HTLC); (b) generating a precursor ion of said DHEA having a mass/charge ratio of $253.10 \pm 0.50$, (c) generating one or more fragment ions of said precursor ion, wherein at least one of said one or more fragment ions comprise a fragment ion selected from the group of fragment ions having a mass/charge ratio of $197.13 \pm 0.50$ and $167.10 \pm 0.50$; and (d) detecting the amount of one or more of said ions generated in step (b) or (c) or both and relating the detected ions to the amount of DHEA in the test sample. In some embodiments, purifying DHEA from a test sample further comprises high performance liquid chromatography (HPLC). In some related embodiments, HTLC and HPLC are configured for on-line processing. In some embodiments, the test sample is body fluid sample; preferably plasma or serum. In some embodiments, the methods have a limit of quantitation greater than or equal to 10 ng/dL but less than or equal to 2000 ng/dL. In some embodiments, the amount of one or more DHEA ions detected by mass spectrometry is related to the presence or amount of DHEA in a test sample by comparison to an internal standard; preferably 2, 2, 4, 6, 6-$d_5$ testosterone. The features of the embodiments listed above may be combined without limitation for use in methods of the present invention.

Methods of the present invention involve the combination of liquid chromatography with mass spectrometry. In preferred embodiments, the liquid chromatography is HPLC. One preferred embodiment utilizes HPLC alone or in combination with one or more purification methods such as for example HTLC and/or protein precipitation and filtration, to purify DHEA in samples. In another preferred embodiment, the mass spectrometry is tandem mass spectrometry (MS/MS).

In certain preferred embodiments of the methods disclosed herein, mass spectrometry is performed in positive ion mode. Alternatively, mass spectrometry is performed in negative ion mode. Various ionization sources, including for example atmospheric pressure chemical ionization (APCI) or electrospray ionization (ESI), may be used in embodiments of the present invention. In certain preferred embodiments, DHEA is measured using APCI in positive ion mode.

In preferred embodiments, DHEA ions detectable in a mass spectrometer are selected from the group consisting of positive ions with a mass/charge ratio (m/z) of 253.10±0.50, 197.10±0.50, and 167.10±0.50. In particularly preferred embodiments, a DHEA precursor ion has m/z of 253.10±0.50, and one or more fragment ions are selected from the group consisting of ions having m/z of 197.10±0.50 and 167.10±0.50.

In preferred embodiments, a separately detectable internal standard is provided in the sample, the amount of which is also determined in the sample. In these embodiments, all or a portion of both the endogenous DHEA and the internal standard present in the sample is ionized to produce a plurality of ions detectable in a mass spectrometer, and one or more ions produced from each are detected by mass spectrometry.

A preferred internal standard is 2, 2, 4, 6, 6-$d_5$ testosterone. In preferred embodiments, the internal standard ions detectable in a mass spectrometer are selected from the group consisting of positive ions with m/z of 294.10±0.50 and 100.06±0.50. In particularly preferred embodiments, an internal standard precursor ion has m/z of 294.10±0.50; and an internal standard fragment ion has m/z of 100.06±0.50.

In preferred embodiments, the presence or amount of the DHEA ion is related to the presence or amount of DHEA in a test sample by comparison to a reference such as 2, 2, 4, 6, 6-$d_5$ testosterone.

In certain preferred embodiments, the limit of quantitation (LOQ) of DHEA is within the range of 10 ng/dL to 2000 ng/dL, inclusive; preferably within the range of 10 ng/dL to 1000 ng/dL, inclusive; preferably within the range of 10 ng/dL to 500 ng/dL, inclusive; preferably within the range of 10 ng/dL to 250 ng/dL, inclusive; preferably within the range of 10 ng/dL to 100 ng/dL, inclusive; preferably within the range of 10 ng/dL to 50 ng/dL, inclusive; preferably within the range of 10 ng/dL to 20 ng/dL, inclusive; preferably about 10 ng/dL.

As used herein, unless otherwise stated, the singular forms "a," "an," and "the" include plural reference. Thus, for example, a reference to "a protein" includes a plurality of protein molecules.

As used herein, "derivatizing" means reacting two molecules to form a new molecule. As used here, the names of derivatized forms of DHEA include an indication as to the nature of derivatization. For example, the sulfate derivative of DHEA is indicated by dehydroepiandrosterone sulfate (DHEA-S) and the oxime derivative of DHEA is indicated by dehydroepiandrosterone oxime (DHEA-O). Dehydroepiandrosterone (DHEA), without indication of derivatization, means underivatized DHEA.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected DHEA parent or daughter ions by mass spectrometry. Relative reduction as this term is used does not require that any substance, present with the analyte of interest in the material to be purified, is entirely removed by purification.

As used herein, the term "test sample" refers to any sample that may contain DHEA. A preferred test sample may be a body fluid or tissue. As used herein, the term "body fluid" means any fluid that can be isolated from the body of an individual. For example, "body fluid" may include blood, plasma, serum, bile, saliva, urine, tears, perspiration, and the like.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, through capillary passageways, or through a single contiguous column of solid support such as monolithic column. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and high turbulence liquid chromatography (HTLC).

As used herein, the term "high performance liquid chromatography" or "HPLC" refers to liquid chromatography in which the degree of separation is increased by forcing the mobile phase under pressure through a stationary phase, typically a densely packed column.

As used herein, the term "high turbulence liquid chromatography" or "HTLC" refers to a form of chromatography that utilizes turbulent flow of the material being assayed through the column packing as the basis for performing the separation. HTLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain HTLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 µm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%. In a preferred embodiment the analytical column contains particles of about 4 µm in diameter.

As used herein, the term "on-line" or "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. Nos. 6,204,500, entitled "Mass Spectrometry From Surfaces;" 6,107,623, entitled "Methods and Apparatus for Tandem Mass Spectrometry;" 6,268,144, entitled "DNA Diagnostics Based On Mass Spectrometry;" 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000).

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated N2 gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heats causes the sample to transfer into the gas phase. The gas phase sample is then drawn into the mass spectrometer.

As used herein, the term "limit of quantification", "limit of quantitation" or "LOQ" refers to the point where measurements become quantitatively meaningful. The analyte response at this LOQ is identifiable, discrete and reproducible with a relative standard deviation (RSD %) of 20% and an accuracy of 80% to 120%.

As used herein, the term "limit of detection" or "LOD" is the point at which the measured value is larger than the uncertainty associated with it. The LOD is the point at which a value is beyond the uncertainty associated with its measurement and is defined as two times the RSD of the mean at the zero concentration.

As used herein, an "amount" of DHEA in a body fluid sample refers generally to an absolute value reflecting the mass of DHEA detectable in volume of body fluid. However, an amount also contemplates a relative amount in comparison to another DHEA amount. For example, an amount of DHEA in a body fluid can be an amount which is greater than a control or normal level of DHEA normally present.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

DETAILED DESCRIPTION OF THE INVENTION

Methods of the present invention are described for measuring the amount of DHEA in a sample. More specifically, mass spectrometric methods are described for detecting and quantifying DHEA in a test sample. The methods may utilize liquid chromatography (LC), most preferably HPLC, to perform a purification of selected analytes, and combine this purification with unique methods of mass spectrometry (MS), thereby providing a high-throughput assay system for detecting and quantifying DHEA in a test sample. The preferred embodiments are particularly well suited for application in large clinical laboratories for automated DHEA assay.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Particularly preferred samples include bodily fluids such as blood, plasma, serum, saliva, cerebrospinal fluid, or a tissue sample. Such samples may be obtained, for example, from a patient; that is, a living person, male or female, presenting oneself in a clinical setting for diagnosis, prognosis, or treatment of a disease or condition. The test sample is preferably obtained from a patient, for example, blood serum or plasma. A sample volume of about 0.5 mL is preferred; however, samples of about 0.1 mL can be analyzed.

The present invention contemplates kits for a DHEA quantitation assay. A kit for an DHEA quantitation assay of the present invention may include a kit comprising an internal standard, in amounts sufficient for at least one assay. Typically, the kits will also include instructions recorded in a tangible form (e.g., contained on paper or an electronic medium) for using the packaged reagents for use in a measurement assay for determining the amount of DHEA.

Calibration and QC pools for use in embodiments of the present invention can be prepared using "stripped" plasma or serum (stripped of DHEA): for example, double charcoal-stripped and delipidized serum. All sources of human or non-human stripped plasma or serum should be checked to ensure that they do not contain measurable amounts of DHEA.

Sample Preparation for Mass Spectrometry

Test samples may be stored below room temperature. Test samples (including controls) stored below room temperature are first allowed to come to room temperature and mixed by mechanical vortex. Internal standard may be added to the test samples at this point.

The samples may then be prepared for mass spectrometry by liquid-liquid or solid-phase extraction. Various methods may be used to enrich DHEA relative to other components in the sample (e.g. protein) prior mass spectrometry, including for example, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

Protein precipitation is one method of preparing a test sample, especially a biological test sample, such as serum or plasma. Such protein purification methods are well known in the art, for example, Polson et al., *Journal of Chromatography B* 2003, 785:263-275, describes protein precipitation techniques suitable for use in methods of the present invention. Protein precipitation may be used to remove most of the protein from the sample leaving DHEA in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis, or alternatively to liquid chromatography and subsequent mass spectrometry analysis. In certain embodiments, the use of protein precipitation such as for example, formic acid protein precipitation, may obviate the need for high turbulence liquid chromatography (HTLC) or other on-line extraction prior to mass spectrometry or HPLC and mass spectrometry.

Accordingly, in some embodiments, protein precipitation, alone or in combination with one or more purification methods, may be used for purification of DHEA prior to mass spectrometry. In these embodiments, the methods may involve (1) performing a protein precipitation of the sample of interest; and (2) loading the supernatant directly onto the LC-mass spectrometer without using on-line extraction or high turbulence liquid chromatography (HTLC). Alternatively, the methods may involve (1) performing a protein precipitation of the sample of interest; and (2) loading the supernatant onto a HTLC using on-line extraction, for further purification prior to mass spectrometry.

One means of sample purification that may be used prior to mass spectrometry is liquid chromatography (LC). Certain methods of liquid chromatography, including high-performance liquid chromatography (HPLC), rely on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select HPLC instruments and columns that are suitable for use with DHEA. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, C-12, or C-18 bonded alkyl groups, preferably C-12 bonded groups. The chromatographic column includes an inlet port for receiving a sample directly or indirectly from coupled SPE column and an outlet port for discharging an effluent that includes the fractionated sample.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted with a hydrophobic column chromatographic system. In certain preferred embodiments, a C-12 analytical column (e.g., a Synergi Max® C12 analytical column from Phenomenex, Inc. (4 µm particle size, 75×3.0 mm), or equivalent) is used. In certain preferred embodiments, HTLC and/or HPLC are performed using HPLC Grade 0.1% aqueous formic acid and 100% methanol as the mobile phases.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, HTLC may be used for purification of DHEA prior to mass spectrometry. In such embodiments, samples may be extracted using an HTLC extraction cartridge which captures the analyte, then eluted and chromatographed on a second HTLC column or onto an analytical HPLC column prior to ionization. For example, samples extraction with an HTLC extraction cartridge may be accomplished with a large particle size (50 µm) packed column. Sample eluted off of this column may then be transferred to an HPLC analytical column, such as a C-12 analytical column, for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

Detection and Quantitation by Mass Spectrometry

In various embodiments, DHEA present in a test sample may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

DHEA may be ionized in positive or negative mode. In preferred embodiments, DHEA is ionized by APCI in positive mode. In related preferred embodiments, DHEA ion is in a gaseous state and the inert collision gas is argon, nitrogen, or helium; preferably argon.

In mass spectrometry techniques generally, after the sample has been ionized, the positively charged or negatively charged ions thereby created may be analyzed to determine a mass-to-charge ratio. Suitable analyzers for determining mass-to-charge ratios include quadrupole analyzers, ion traps analyzers, and time-of-flight analyzers. The ions may be detected using several detection modes. For example, selected ions may be detected, i.e. using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g., 100 to 1000 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of DHEA. Methods of generating and using such standard curves are well known in the art and one of ordinary skill is capable of selecting an appropriate internal standard. For example, an isotopically labeled steroid may be used as an internal standard; in certain preferred embodiments the standard is 2, 2, 4, 6, 6-$d_5$ testosterone. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activation dissociation is often used to generate the fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In particularly preferred embodiments, DHEA is detected and/or quantified using MS/MS as follows. The samples are subjected to liquid chromatography, preferably HTLC (including solid phase extraction followed by HPLC); the flow of liquid solvent from the chromatographic column enters the heated nebulizer interface of an MS/MS analyzer; and the solvent/analyte mixture is converted to vapor in the heated tubing of the interface. The analyte (e.g., DHEA), contained in the nebulized solvent, is ionized by the corona discharge needle of the interface, which applies a large voltage to the nebulized solvent/analyte mixture. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios of DHEA. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral argon gas molecules and fragment. This process is called collision activated dissociation (CAD). The fragment ions generated are passed into quadrupole 3 (Q3), where the fragment ions of DHEA are selected while other ions are eliminated.

The methods may involve MS/MS performed in either positive or negative ion mode; preferably positive ion mode. Using standard methods well known in the art, one of ordinary skill is capable of identifying one or more fragment ions of a particular precursor ion of DHEA that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte of interest. In certain embodiments, the area under the curves, or amplitude of the peaks, for fragment ion(s) and/or precursor ions are measured to determine the amount of DHEA. As described above, the relative abundance of a given ion may be converted into an absolute amount of the original analyte, e.g., DHEA, using calibration standard curves based on peaks of one or more ions of an internal molecular standard, such as 2, 2, 4, 6, 6-$d_5$ testosterone.

The following examples serve to illustrate the invention. These examples are in no way intended to limit the scope of the methods.

EXAMPLES

Example 1

Serum Sample and Reagent Preparation

Plasma samples were prepared by collecting blood in a Vacutainer tube with no additives and allowed to clot for about 30 minutes at room temperature. Samples were then centrifuged and the serum separated from the cells. Samples that exhibited gross hemolysis were excluded.

Two DHEA stock solutions were prepared. A DHEA stock standard solution of 1 mg/mL in methanol was prepared in a volumetric flask. A portion of the DHEA stock standard solution was then diluted 100× to prepare a DHEA intermediate stock standard solution of 1,000,000 ng/dL in methanol. The intermediate stock standard solution was used to prepare two working standards: a DHEA working standard of 20,000 ng/dL in methanol, and a DHEA working standard of 10,000 ng/dL in stripped serum.

2, 2, 4, 6, 6-$d_5$ testosterone (CDN Isotopes, Cat. No. D-4000, or equivalent) was used to prepare a 1.0 mg/mL in deuterated methanol 2, 2, 4, 6, 6-$d_5$ testosterone internal standard stock solution, which was used to prepare a 10,000 ng/dL in deuterated methanol 2, 2, 4, 6, 6-$d_5$ testosterone intermediate internal standard stock solution: 100 μL of the 2, 2, 4, 6, 6-$d_5$ testosterone internal standard stock solution was diluted to volume with DI water in a 10 mL volumetric flask. The 2, 2, 4, 6, 6-$d_5$ testosterone intermediate internal standard stock solution was used to prepare 10 ng/mL in water 2, 2, 4, 6, 6-$d_5$ testosterone intermediate internal standard working solution: 200 μL 2, 2, 4, 6, 6-$d_5$ testosterone intermediate internal standard stock solution was diluted to volume with DI water in a 200 mL volumetric flask

Example 2

Extraction of DHEA from Samples Using Liquid Chromatography

Room temperature standards, controls, and patient samples were prepared for liquid chromatography (LC) by first mixing by mechanical vortex.

200 μL of each vortexed standard, control, and patient sample was then transferred to a well of a 96-well plate. 400 μL of 20% formic acid and 100 μL of 10 ng/mL 2, 2, 4, 6, 6-$d_5$ testosterone internal standard were then added to each. The plates were then vortexed and incubated at room temperature for 30 minutes before being loaded into an autosampler drawer.

Sample injection was performed with a Cohesive Technologies Aria TLX-1 HTLC system using Aria OS V 1.5 or newer software. An autosampler wash solution was prepared using 60% acetonitrile, 30% isopropanol, and 10% acetone (v/v).

The HTLC system automatically injected 100 μL of the above prepared samples into a TurboFlow column (50×1.0 mm, 50 μm C18 column from Cohesive Technologies) packed with large particles. The samples were loaded at a high flow rate (5.0 mL/min, loading reagent 0.1% formic acid) to create turbulence inside the extraction column. This turbulence ensured optimized binding of DHEA to the large particles in the column and the passage of residual protein and debris to waste.

Following loading, the flow direction was reversed and the sample eluted off to the analytical column (Phenomenex, Inc. analytical column, Synergi Max® C12 column, 4 μm particle size, 75×3.0 mm). A binary HPLC gradient was applied to the analytical column, to separate DHEA from other analytes contained in the sample. Mobile phase A was 0.1% formic acid and mobile phase B was 100% methanol. The HPLC gradient started with a 5% organic gradient which ramped to 95% in approximately 5.5 minutes. The separated sample was then subjected to MS/MS for quantitation of DHEA.

The specificity of the DHEA against similar analytes was determined for the following compounds (each at a concentration of 100 ng/dL in stripped serum): testosterone, estrone, estradiol, estriol, pregnenolone, DHEA-S, androstenedione, and 17-OH pregnenolone. No significant interference for any of these compounds was observed.

Example 3

Detection and Quantitation of DHEA by MS/MS

MS/MS was performed using a Finnigan TSQ Quantum Ultra MS/MS system (Thermo Electron Corporation). The following software programs all from ThermoElectron were used in the Examples described herein: Quantum Tune Master V 1.2 or newer, Xcalibur V 1.4 SR1 or newer, TSQ Quantum 1.4 or newer, and LCQuan V 2.0 with SP1 or newer. Liquid solvent/analyte exiting the analytical column flowed to the heated nebulizer interface of a Thermo Finnigan MS/MS analyzer. The solvent/analyte mixture was converted to vapor in the heated tubing of the interface. Analytes in the nebulized solvent were ionized by APCI.

Ions passed to the first quadrupole (Q1), which selected ions with a mass to charge ratio of 253.10±0.50 m/z. Ions entering Quadrupole 2 (Q2) collided with argon gas to generate ion fragments, which were passed to quadrupole 3 (Q3) for further selection. Simultaneously, the same process using isotope dilution mass spectrometry was carried out with an internal standard, 2, 2, 4, 6, 6-$d_5$ testosterone. The following mass transitions were used for detection and quantitation during validation on positive polarity.

TABLE 1

| Mass Transitions for DHEA (Positive Polarity) | | |
|---|---|---|
| Analyte | Precursor Ion (m/z) | Product Ion (m/z) |
| DHEA | 253.10 | 167.10 and 197.13 |
| 2,2,4,6,6-$d_5$ testosterone (internal standard) | 294.10 | 100.06 |

Figure 1A:
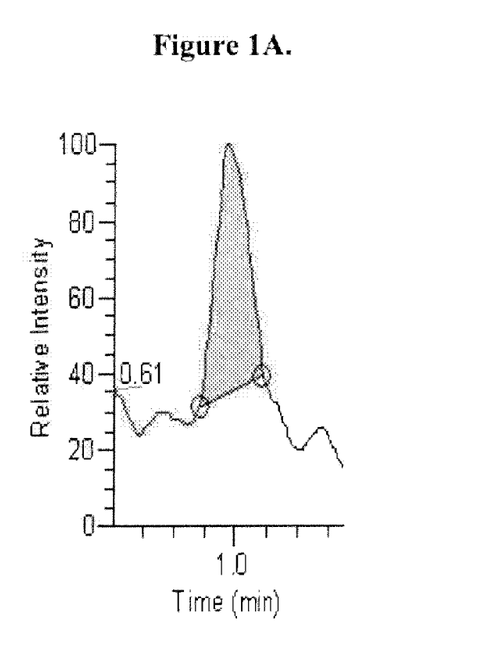
FIGS. 1A and 1B shows exemplary mass chromatograms of DHEA and 2, 2, 4, 6, 6-$d_5$ testosterone (internal standard), respectively. Details are discussed in Example 3.
Figure 1B:
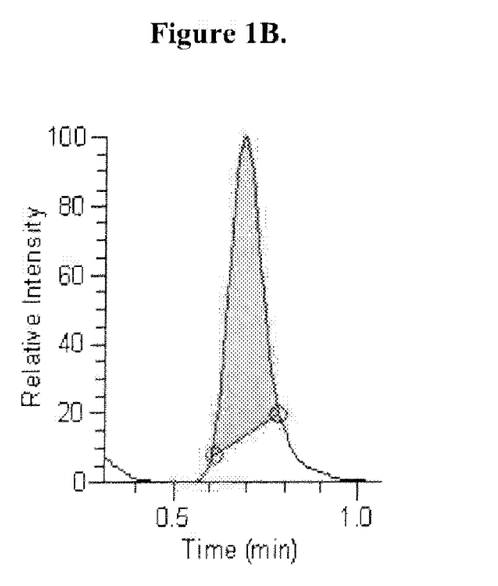

Exemplary chromatograms for DHEA and 2, 2, 4, 6, 6-$d_5$ testosterone (internal standard) are found in FIG. 1.

Example 4

Intra-Assay and Inter-Assay Precision and Accuracy

Three quality control (QC) pools were prepared from analyte-stripped human serum (Golden West Biologicals, Temecula, Calif.) spiked with DHEA to a concentration of 30, 300, and 900 ng/dL, to cover the presumptive reportable range of the assay.

Ten aliquots from each of the three QC pools were analyzed in a single assay to determine the coefficient of variation (CV (%)) of a sample within an assay. The following values were determined:

TABLE 2

| Intra-Assay Variation and Accuracy | | | |
|---|---|---|---|
|  | Level I (30 ng/dL) | Level II (300 ng/dL) | Level III (900 ng/dL) |
| Mean (ng/dL) | 28.87 | 296.73 | 874.12 |
| Standard Deviation (ng/dL) | 3.90 | 15.42 | 28.41 |
| CV (%) | 13.51% | 5.19% | 3.25% |
| Accuracy (%) | 96.23% | 98.91% | 97.12% |

Ten aliquots from each of the three QC pools were assayed over ten days to determine the coefficient of variation (CV (%)) between assays. The following values were determined:

TABLE 3

| Inter-Assay Variation and Accuracy | | | |
|---|---|---|---|
|  | Level I (30 ng/dL) | Level II (300 ng/dL) | Level III (900 ng/dL) |
| Mean (ng/dL) | 29.98 | 295.32 | 926.92 |
| Standard Deviation (ng/dL) | 4.27 | 22.83 | 66.17 |
| CV (%) | 14.26% | 7.73% | 7.13% |
| Accuracy (%) | 99.96% | 98.44% | 102.99% |

Example 5

Analytical Sensitivity: Limit of Detection (LOD) and Limit of Quantitation (LOQ)

Figure 2:
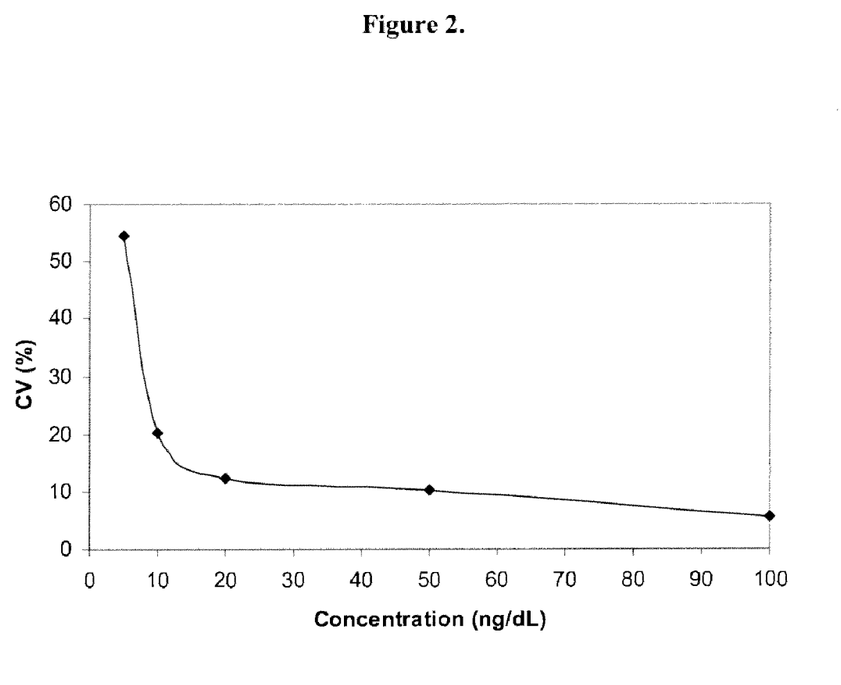
FIG. 2 shows a plot of the coefficient of variation of assays of five standards each assayed five times to determine the limit of quantitation of the DHEA assay. Details are discussed in Example 5.

The LOQ is the point where measurements become quantitatively meaningful. The analyte response at this LOQ is identifiable, discrete and reproducible with a precision of 20% and an accuracy of 80% to 120) %. The LOQ was determined by assaying analyte-stripped serum specimens spiked with DHEA concentrations of 5, 10, 20, 50, and 100 ng/dL (five replicates at each level) then determining the CV. The results were plotted (as seen in FIG. 2) and the LOQ was determined from the curve to be 10.0 ng/dL.

The LOD is the point at which a value is beyond the uncertainty associated with its measurement and is defined as two standard deviations from the zero concentration. To determine the LOQ for the DHEA assay, blank samples of charcoal-stripped serum were run in ten replicates. The results of these assays were statistically analyzed with a mean value of 1.43 ng/dL, a SD of 0.44, and a CV of 30.6%. Thus, the LOD for the DHEA was 2.30 ng/dL.

Example 6

Assay Reportable Range and Linearity

Figure 3:
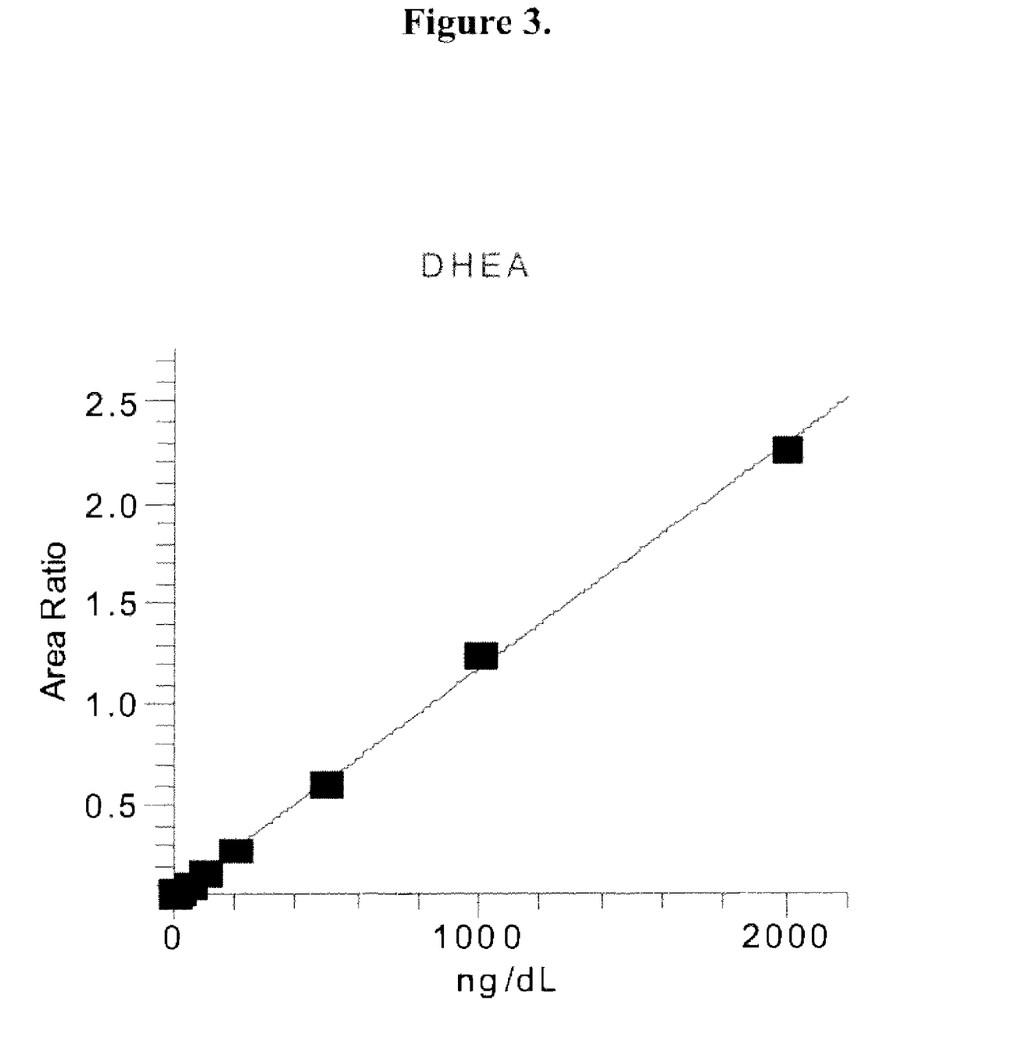
FIG. 3 shows the linearity of the quantitation of DHEA in serially diluted stock samples using an LC-MS/MS assay. Details are described in Example 6.

To establish the linearity of DHEA detection in the assay, three separate assays, each including one blank assigned as zero standard and eight spiked serum standards at concentrations ranging from a zero standard to 2000 ng/dL were performed. The correlation value of the concentration range tested (0 to 2000 ng/dL) was greater than 0.995. A graph showing the linearity of the standard curve up to 2000 ng/dL is shown in FIG. 3.

Example 7

Matrix Specificity

Matrix specificity was evaluated by diluting patient serum samples three-fold and five-fold with the following matrices: analyte-stripped serum (charcoal stripped serum, Cat. No. SP1070, Golden West Biologicals, Inc.), normal human defibrinated serum (Cat. No. 1101-00, Biocell Labs, Carson, Calif. 90746, or equivalent), and deionized (DI) water. Four serum samples were spiked with the following concentrations of DHEA: 119.3 ng/dL, 72.4 ng/dL, 913 ng/dL, and 303 ng/dL. The spiked serums were then diluted 3× and 5× with the above matrices and analyzed. The study indicated that stripped serum is preferred for dilution of samples with analyte values above the linear range. The results of this study are presented in Table 4.

TABLE 4

| Matrix Specificity of DHEA | | | | | |
|---|---|---|---|---|---|
|  | Dilutions | Expected Concentration (ng/dL) | Stripped Serum (ng/dL) | Biocell Serum (ng/dL) | DI Water (ng/dL) |
| Sample 1 | — | 119.3 | | | |
|  | 3× | 39.8 | 42.78 | 103.1 | 38.62 |
|  | 5× | 23.86 | 19.13 | 55.58 | 12.61 |
| Sample 2 | — | 72.4 | | | |
|  | 3× | 24.1 | 24.10 | 65.66 | 18.45 |
|  | 5× | 14.47 | 16.60 | 52.98 | 10.52 |
| Sample 3 | — | 913 | | | |
|  | 3× | 304.62 | 307.28 | 376.11 | 351.93 |
|  | 5× | 182.77 | 163.77 | 220.63 | 196.33 |
| Sample 4 | — | 303 | | | |
|  | 3× | 101.15 | 84.89 | 132.9 | 118.63 |
|  | 5× | 60.69 | 68.6 | 81.25 | 58.69 |

Example 8

Recovery

Pooled human serum or plasma from specimens older than one month were used. The pool was split into three groups spiked with DHEA to a concentration of 254, 470, and 1010 ng/dL.

A recovery study of these DHEA spiked samples was performed (in quadruplicate for each concentration). Absolute recovery was calculated by dividing the DHEA concentration detected in the pooled samples by the expected DHEA concentration in samples. The mean recoveries were 89.22%, 92.19%, and 90.33%, respectively, giving an overall recovery of 90.58%. All recoveries were acceptable, i.e., within the range of 80% to 120%.

Example 9

Specimen Studies

Specimens derived from sample collection tubes with no additives (for serum), serum separator tubes (SST), EDTA tubes, or sodium heparin tubes (50 samples each, 25 from males and 25 from females) were tested for the applicability of the instant methods to various sample types.

Figure 4A:
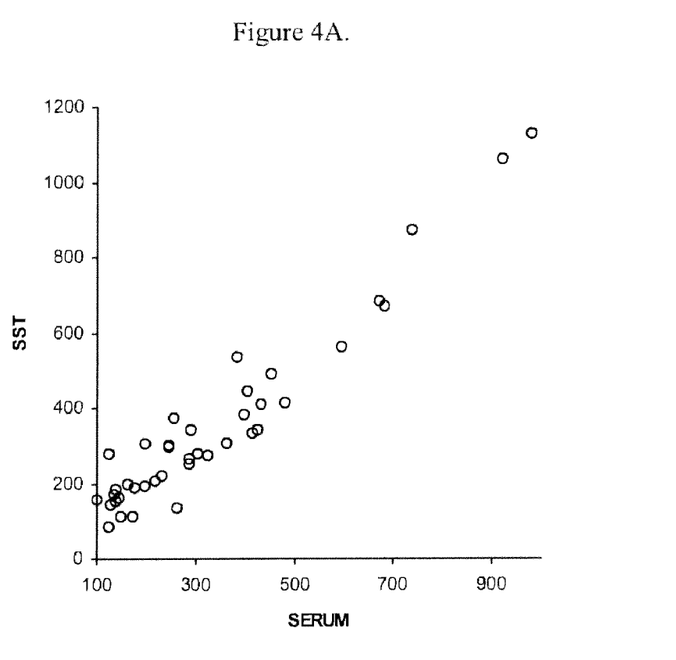
FIGS. 4A-C show the comparison of DHEA determined in serum samples and samples from serum separator tubes (SST), EDTA tubes, and sodium heparin tubes. Details are described in Example 9.
Figure 4B:
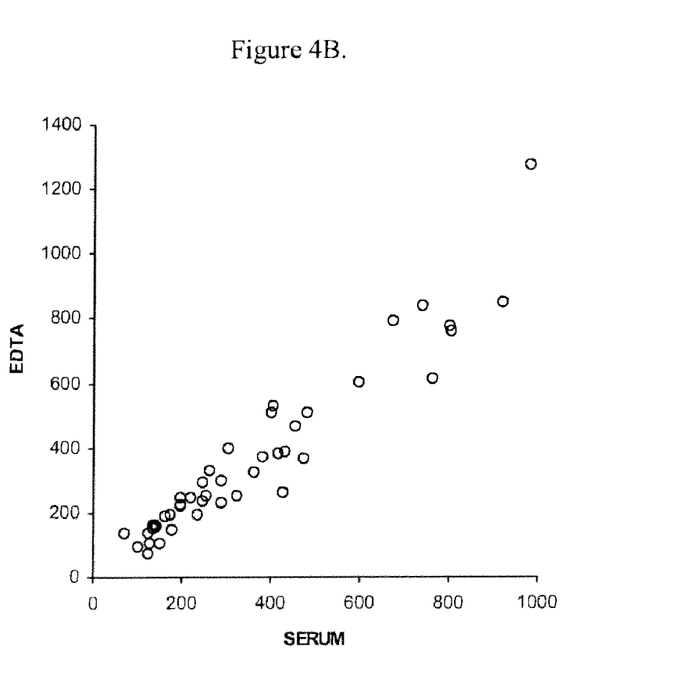
Figure 4C:
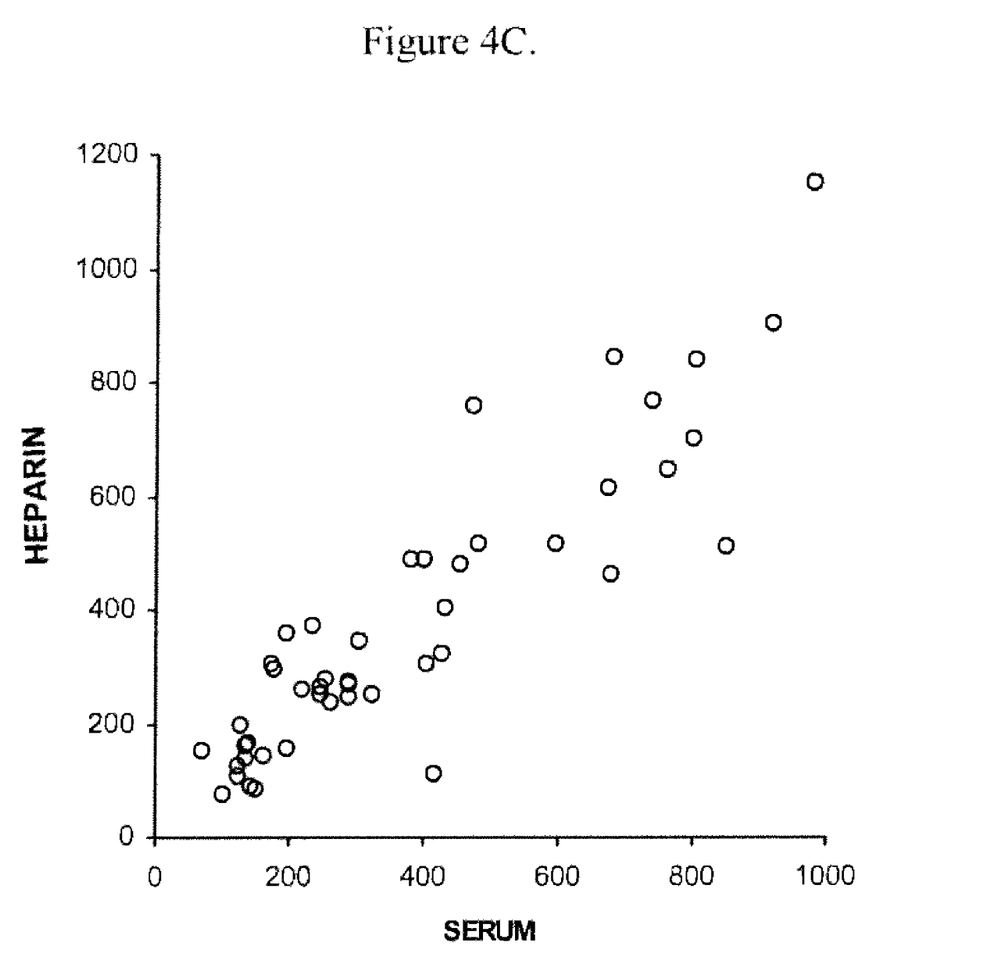

FIGS. 4A-C show comparisons of the DHEA determination for serum samples from collection tubes with no additives and samples from the other collection tubes listed above (SST, EDTA, and sodium heparin). While DHEA was detectable in all tested sample types, the DHEA levels detected in samples from EDTA tubes were most similar to DHEA levels detected in samples from collection tubes with no additives (see FIG. 4B).

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of underivatized dehydroepiandrosterone (DHEA) in a test sample, said method comprising:
   a. ionizing DHEA from said test sample to produce one or more DHEA ions detectable by mass spectrometry, wherein said ions comprise one or more ions selected from the group consisting of ions with a mass/charge ratio of 253.10±0.50, 197.13±0.50, and 167.10±0.50; and
   b. detecting the amount of one or more DHEA ions by mass spectrometry, wherein the amount of the DHEA ion(s) is related to the amount of underivatized DHEA in said test sample.

2. The method of claim 1, wherein said mass spectrometry is tandem mass spectrometry.

3. The method of claim 1, further comprising purifying underivatized DHEA in said test sample prior to ionizing DHEA.

4. The method of claim 3, wherein said purifying comprises purifying with liquid chromatography.

5. The method of claim 4, wherein said liquid chromatography comprises high performance liquid chromatography (HPLC).

6. The method of claim 3, wherein said purifying comprises purifying with high turbulence liquid chromatography (HTLC) followed by high performance liquid chromatography (HPLC).

7. The method of claim 6, wherein said HTLC and said HPLC are configured for on-line processing.

8. The method of claim 1, wherein said test sample is a body fluid.

9. The method of claim 1, wherein said test sample is plasma or serum.

10. The method of claim 1, wherein said ionizing comprises generating a precursor ion with a mass/charge ratio of 253.10±0.50 and generating one or more fragment ions selected from the group consisting of ions with a mass/charge ratio of 197.13±0.50 and 167.10±0.50.

11. The method of claim 1, wherein said method has a limit of quantitation within the range of 10 ng/dL to 2000 ng/dL, inclusive.

12. A method for determining the amount of underivatized dehydroepiandrosterone (DHEA) in a test sample by mass spectrometry, said method comprising:
   a. purifying DHEA in said test sample with high turbulence liquid chromatography (HTLC);
   b. ionizing DHEA from said test sample to produce one or more DHEA ions detectable by mass spectrometry; and
   c. detecting the amount of one or more DHEA ions by mass spectrometry, wherein the amount of the DHEA ion(s) is related to the amount of underivatized DHEA in said test sample.

13. The method of claim 12, wherein said mass spectrometry is tandem mass spectrometry.

14. The method of claim 12, wherein said purifying further comprises purifying with high performance liquid chromatography (HPLC).

15. The method of claim 14, wherein said HTLC and said HPLC are configured for on-line processing.

16. The method of claim 12, wherein said test sample is a body fluid sample.

17. The method of claim 12, wherein said test sample is plasma or serum.

18. The method of claim 12, wherein the one or more DHEA ions detectable by mass spectrometry comprise one or more ions selected from the group consisting of ions with a mass/charge ratio of 253.10±0.50, 197.13±0.50, and 167.10±0.50.

19. The method of claim 12, wherein said ionizing comprises generating a precursor ion with a mass/charge ratio of 253.10±0.50 and generating one or more fragment ions selected from the group consisting of ions with a mass/charge ratio of 197.13±0.50 and 167.10±0.50.

20. The method of claim 12, wherein said method has a limit of quantitation within the range of 10 ng/dL to 2000 ng/dL, inclusive.

21. A method for determining the amount of underivatized dehydroepiandrosterone (DHEA) in a test sample by tandem mass spectrometry said method comprising:
  a. purifying DHEA in said test sample by high turbulence liquid chromatography (HTLC);
  b. generating a precursor ion of said DHEA having a mass/charge ratio of 253.10±0.50;
  c. generating one or more fragment ions of said precursor ion, wherein at least one of said one or more fragment ions comprise a fragment ion selected from the group of fragment ions having a mass/charge ratio of 197.13±0.50 and 167.10±0.50; and
  d. detecting the amount of one or more of said ions generated in step (b) or (c) or both and relating the detected ions to the amount of underivatized DHEA in said test sample.

22. The method of claim 21, wherein purifying DHEA in said test sample comprises high performance liquid chromatography (HPLC).

23. The method of claim 22, wherein said HTLC and said HPLC are configured for on-line processing.

24. The method of claim 21, wherein said test sample is a body fluid sample.

25. The method of claim 21, wherein said test sample is plasma or serum.

26. The method of claim 21, wherein said method has a limit of quantitation within the range of 10 ng/dL to 2000 ng/dL, inclusive.

* * * * *

UNITED STATES PATENT AND TRADEMARK OFFICE
CERTIFICATE OF CORRECTION

PATENT NO.        : 7,893,399 B2
APPLICATION NO.   : 12/207428
DATED             : February 22, 2011
INVENTOR(S)       : Amit Ghoshal, Nigel J. Clarke and Richard E. Reitz It is certified that error appears in the above-identified patent and that said Letters Patent is hereby corrected as shown below:

Column 5, line 52, delete the phrase ""m z"" and replace with --"m/z"--.

Column 11, line 43, delete the phrase "mass charge" and replace with --mass/charge--.

Signed and Sealed this
Twenty-seventh Day of September, 2011

David J. Kappos
*Director of the United States Patent and Trademark Office*